United States Patent [19]

Jones et al.

[11] Patent Number: 4,849,522

[45] Date of Patent: Jul. 18, 1989

[54] NOVEL ALKOXYIMINO ETHER DERIVATIVES OF 5-ACYL-2(1H)-PYRIDINONES

[75] Inventors: Winton D. Jones; Richard C. Dage; Richard A. Schnettler, all of Cincinnati, Ohio

[73] Assignee: Merrell Dow Pharmaceuticals, Cincinnati, Ohio

[21] Appl. No.: 166,147

[22] Filed: Mar. 10, 1988

Related U.S. Application Data

[60] Division of Ser. No. 834,692, Feb. 28, 1986, Pat. No. 4,732,982, which is a continuation of Ser. No. 548,398, Nov. 3, 1983, abandoned.

[51] Int. Cl.$^4$ ............................................ C07D 211/94
[52] U.S. Cl. .................................... 546/288; 546/296; 546/297; 546/300; 546/278
[58] Field of Search ............... 546/288, 296, 297, 300, 546/278

[56] References Cited

U.S. PATENT DOCUMENTS 3,190,800  6/1965  Furst .................................. 514/354
4,305,948 12/1981  Gruett et al. ...................... 546/257

FOREIGN PATENT DOCUMENTS 0089022  9/1983  European Pat. Off. .
2738589  3/1978  Fed. Rep. of Germany .
3005069  8/1981  Fed. Rep. of Germany .
1169074 10/1969  United Kingdom .
2040287  8/1980  United Kingdom .

Primary Examiner—Jane T. Fan
Attorney, Agent, or Firm—Michael J. Sayles; Stephen L. Nesbitt

[57] ABSTRACT

This invention relates to alkoxyimino ether derivatives of 5-acyl-2(1H)-pyridinones and to their use as cardiotonic agents useful in treating cardiac failure, and to the process useful in the preparation thereof.

6 Claims, No Drawings

NOVEL ALKOXYIMINO ETHER DERIVATIVES OF 5-ACYL-2(1H)-PYRIDINONES

This is a divisional of application Ser. No. 834,692, filed Feb. 28, 1986, now issued as U.S. Pat. No. 4,732,982 which is a continuation of application Ser. No. 548,398, filed Nov. 3, 1983, now abandoned.

This invention relates to alkoxyimino ether derivatives of 5-acyl-2(1H)-pyridinones and to their use as cardiotonic agents useful in treating cardiac failure, and to the process useful in the preparation thereof.

More specifically, this invention relates to the pharmaceutically active alkoxyimino ethers having the formula

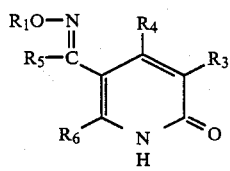

I and the pharmaceutically acceptable salts thereof wherein $R_1$ is $C_{1-10}$ alkyl, $R_3$ is H, lower alkyl, —C≡N, $NH_2$, $CONH_2$ and COOR with R being hydrogen or lower alkyl, $R_4$ is hydrogen or lower alkyl, $R_5$ is $C_{1-10}$ alkyl, phenyl, X-substituted phenyl, pyridyl, thienyl, furyl, pyrrolyl and OR wherein R is hydrogen or lower alkyl, and X is lower alkyl, lower alkoxy, lower alkylthio, lower alkyl sulfone, lower alkyl sulfoxide, halogen, nitro, lower alkanoyl, alkoxy carbonyl, carboxy, cyano, $NH_2$, $CONH_2$, COOR with R being hydrogen or lower alkyl, amidino, imidazol-2-yl, and $CF_3$, and $R_6$ is hydrogen or $R_5$.

These compounds are useful as cardiotonics in the treatment of cardiac failure and other conditions requiring strengthening of heart action with a cardiotonic agent.

As used herein, the term "alkyl" includes straight, branched-chain or cyclized hydrocarbyl radicals. Representative hydrocarbyls are radicals such as methyl, ethyl, propyl, isopropyl, cyclocyclopropyl, n-butyl, isobutyl, t-butyl, cyclobutyl, pentyl and hexyl, septyl, octyl, nonyl and decyl, with methyl and n-butyl being preferred. The term "X"-substituted phenyl include those substituents preferably located in the para position but includes the ortho and meta substituted compounds. The term "lower" when used to modify alkyl, alkoxy, alkylthio embrace those radicals having one to six carbon atoms. Inclusive of other "X" radicals are alkoxycarbonyl (—COO lower alkyl), lower alkanoyl (—CO—lower alkyl), amidino (—C(=NH)—NH$_2$), imidazol-2-yl

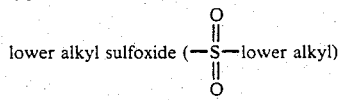, lower alkyl sulfone (—S(=O)$_2$—lower alkyl),

-continued lower alkyl sulfoxide (—S(=O)—lower alkyl)

and halogen preferably includes chloro and bromo but is embrasive of all members. The term "pyridyl" includes 2-, 3-, and 4-pyridyl, "furanyl" include 2- and 3-furanyl, "thienyl" includes 2- and 3-thienyl, and "pyrryl" includes 2- and 3-(1H)-pyrryl.

The compounds of formula I are useful both in the free base form and in the form of acid addition salts with both forms being within the purview of this invention. The acid addition salts are simply a more convenient form for use and, in practice, use of the salt amounts to use of the free base. The acids which can be used include those which produce, when combined with the free base, pharmaceutically acceptable salts, that is salts whose anions are relatively inocuous to the animal organism in pharmaceutical doses of the salts. In practice, it is convenient to form sulfate, phosphate, methansulfate or lactate salts. Others are those derived from mineral acids (e.g., hydrochloric), and organic acids such as acetic acid, citric acid, tartaric acid, ethanesulfonic acid, benzenesulfonic acid, p-toluenesulfonic acid and the like. The acid salts are prepared by standard techniques such as by dissolving the free base in aqueous or aqueous-alcohol solution or other suitable solvents containing the appropriate acid and isolating by evaporating the solution, or by reacting the free base and in an organic solvent in which case the salt separates directly or can be obtained by concentration of the solution.

In general, the compounds of this invention are prepared by standard techniques analogously known in the art. A convenient synthesis for preparing the compounds of formula I conveniently involves the reaction of a 5-acyl-2(1H)-pyridinone (II) with the appropriate alkoxyamine, preferably in the form of an acid addition salt, according to standard oximation reaction conditions. In effecting the oximination, the alkoxyamine is contacted with a base (e.g., pyridine) to form an anion which is then condensed with the 5-acyl-2(1H)-pyridinone (II) by heating the reactants together in an inert solvent. The reaction proceeds well at temperatures between room temperature and the reflux temperature of the reaction mixture. Reaction at reflux is preferred wherein any art-recognized solvent, such as ethanol, may be utilized.

The foregoing reaction is depicted as follows:

Reaction Scheme A:

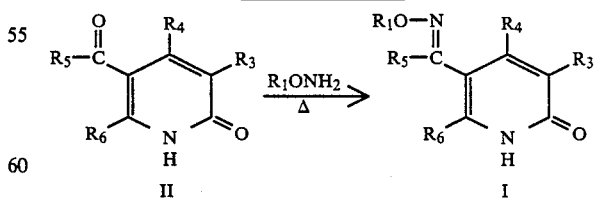

wherein $R_1$, $R_3$, $R_4$, $R_5$ and $R_6$ are as defined. Of course in those instances wherein the 5-acyl-2(1H)pyridinone bears substituents which would be unstable under the reaction conditions, then such substituent-bearing compounds would first be modified. Then, upon completion of the oximination reaction, the desired compounds may be obtained. Such procedures are well known and represent standard techniques well known in the art.

The 5-acyl-2(1H)pyridinone intermediates (II) are prepared by standard techniques analogously known in the art. A preferred synthesis for preparing these intermediates conveniently involves the reaction of an appropriate 1-$R_5$-3-$R_6$-2-(1-dimethylamino-1-$R_4$-methylidenyl)-1,3-propanedione (III) with an appropriately $R_3$ substituted acetoacetamide (IV) according to standard Michael addition addition reaction conditions. Preferably, the substituted acetamide is reacted with sodium hydride, under argon in an inert organic solvent, (e.g., tetrahydrofuran) to form an anion which is then condensed with the diketone (III) by heating the reactants together in an inert organic solvent, preferably tetrahydrofuran and the like. Preferably, the temperature of the reaction is about 50° C. although the reaction proceeds well at temperatures between room temperature and 100° C. Heating is effected over a period of several hours although it is preferred to allow the reaction to proceed overnight. When $R_5$ and $R_6$ are not the same a mixture of products are obtained which are separated quite nicely by flash chromatography wherein the reaction product mixture is admixed with 60–200 mesh silica gel and the column is eluted with an appropriate solvent system (e.g., 35% ethylacetate —65% methylene chloride). The fractions of eluate are monitored by thin layer chromatography.

The foregoing reaction is depicted as follows:

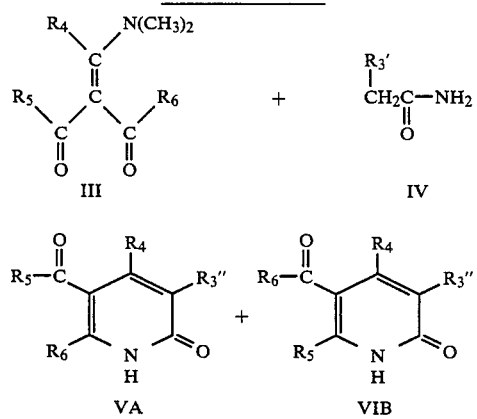

Reaction Scheme B:

wherein $R_4$, $R_5$ and $R_6$ are as previously defined, $R_3''$ is cyano, —$CO_2H$, lower alkyl or $NH_2$; $R_3'$ is cyano, —$CO_2H$, lower alkyl or —N=CH phenyl.

The 1-$R_5$-3$R_6$-2-[(1-dimethylamino)alkylidenyl]-1,3-propanediones (III) are readily prepared by condensing the appropriate $R_5$, $R_6$-1,3-propanediones with the appropriately $R_4$ substituted N,N-dialkylamino-dialkoxy methane (e.g., dimethylformamide acetals) according to standard condensation reaction conditions such as, for example, contacting equimolar quantities of the reactants together, optionally in an inert organic solvent and stirring the mixture for 1–12 hours at about room temperature. This reaction is depicted as follows:

Reaction Scheme C:

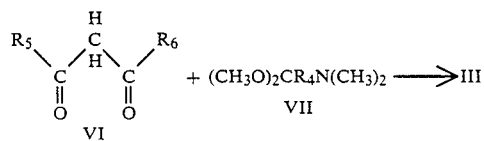

wherein $R_4$, $R_5$ and $R_6$ are as previously defined.

In those instances, wherein X is other than lower alkyl, hydroxy, alkoxy, halogen, nitro, cyano, amino, and $R_3$ is other than cyano, it is preferred to prepare a compound of formula I wherein X is cyano, and then, by the use of standard techniques, convert the cyano moiety to the desired substituents. For example, the cyano moiety may be converted to a carboxyl moiety by hydrolyzing the nitrile with 6N hydrochloric acid, sulfuric and/or other mineral acids under standard conditions such as by heating at reflux temperatures for about 12–24 hours. The carboxyl moiety may be converted to an alkoxycarbonyl moiety by the standard Fisher esterification procedure such as by heating the carboxy-containing compounds with an appropriate alcohol in the presence of an acid, e.g., 3% hydrochloric acid. The carboxamido-containing compounds may be prepared by converting the alkoxycarbonyl moiety by heating the esters in the presence of ammonia or an appropriate amine, preferably in a pressure bomb at about 100°–150° C. in an inert solvent, e.g., benzene, toluene and the like. Alternatively, the carboxamido moiety may be prepared by hydrolizing a nitrile with concentrated sulfuric acid by heating on a steam bath at temperatures of about 50°–100° C. In those instances wherein $R_3$ is cyano, it is preferred to have the ultimately desired X substituent on the phenyl ring prior to the Michael addition reaction between the 1-$R_{5-3}$-$R_{6-2}$-(1-dimethylamino-1-$R_4$-methylidenyl)-1,3-propanedione and the cyano substituted acetamide.

In those instances wherein X is imidazol-2-yl, such compounds are prepared by a condensation reaction wherein the nitrile is heated to from about 150°–200° C. with ethylene diamine for about 2 hours. The amidino compounds are prepared from corresponding nitriles wherein the nitrile is converted to an imino ether which is converted to the amidino moiety by treating the imino ether with ammonia in alcohol at temperatures of about 0° C. room temperature. The sulfones and sulfoxides may be prepared from the alkylthio moiety by standard oxidation procedures.

In those instances wherein the $R_3$ substituent is hydrogen, it is preferred to chemically remove a cyano moiety from a compound of formula I by standard techniques such as by conversion of the cyano moiety to a carboxyl radical by treatment with a strong acid and then the compound is decarboxylated. Alternatively, the carboxyl radical may be converted to an alkyl moiety by standard Grignard reaction conditions.

The preparation of the compounds of formula I may be illustrated by the following specific examples.

PREPARATION OF INTERMEDIATE 1-R$_5$-3R$_6$-2-(1-DIALKYLAMINO-1-R$_4$ METHYLIDINYL)-1,3-PROPANDIONES

EXAMPLE 1

2-Dimethylaminomethylenyl-1-phenyl-1,3-butandione

A mixture of 1-benzoylacetone (24.00 g, 0.15 mole) and dimethylformamide dimethylacetal were stirred overnight at room temperature under argon. The resulting reddish-colored mixture was concentrated on the rotary evaporator, then dissolved in THF (tetrahydrofuran). The resulting solution was stirred and heated to boiling and slowly diluted with hexane. At the point of turbidity heating was discontinued. An orange gum precipitated and rapidly solidified. The mixture was chilled in an ice bath and filtered yielding 25.25 g (78%) of 2-(dimethylamino)-1-phenyl-1,3-butanedione m.pt. 72°–74° C.

EXAMPLE 2

3-[(Dimethylamino)methylenyl]-2,4-pentanedione

A mixture of dimethylformamide dimethyl acetal (16.68 g, 0.136 mole) and 2,4-pentanedione (13.65 g, 136 mole) was stirred overnight at room temperature under argon. The resulting red oil was concentrated on the rotary evaporator to yield 20.15 g (86%) of 3-[(Dimethylamino)methylenyl]-2,4-pentanedione.

EXAMPLE 3

3-[(Dimethylamino)Methylene]-2,4-Octanedione

A mixture of 2,4-octanedione (7.11 g, 0.50 mole) and dimethylformamide dimethylacetal (7.15 g, 0.60 mole) was stirred overnight at room temperature under argon. The resulting red oil was concentrated on the rotary evaporation then distilled on the kugelrohr at −15 mm, 140°–155° C. to yield 8.60 g (87%) of 3-[(dimethylamino)methyleno]-2,4-octanodione.

EXAMPLE 4

4-[(Dimethylamino)methylenyl]-3,5-heptanedione

A mixture of 3,5-heptanedione (6.41 g, .050 mole) and dimethylformamide dimethylacetal (6.27 g, .053 mole) were stirred at room temperature overnight under argon. The resulting red liquid was concentrated on the rotary evaporator to yield 8.60 g (99%) of 4-[(Dimethylamino)methylenyl]-3,5-heptanedione.

In a similar manner, by substituting the 1,3-propandiones of the foregoing examples with the appropriately substituted analogs thereof and by substantially following the procedures there is produced the following intermediates:

1-(4-cyanophenyl)-2-(dimethylaminomethylenyl)-1,3-butandione,
1-(4-chlorophenyl)-2-(dimethylaminomethylenyl)-1,3-butandione,
1-(4-pyridyl)-2-(dimethylaminomethylenyl)-1,3-butandione,
1-(2-thienyl)-2-(dimethylaminomethylenyl)-1,3-butandione,
1-[2-(1-H-pyrryl)]-2-(dimethylaminomethylenyl)-1,3-butandione,
1-(3-furanyl)-2-(dimethylaminomethylenyl)-1,3-butandione,
1-(4-methoxyphenyl)-2-(dimethylaminomethylenyl)-1,3-butandione,
1-(4-methylphenyl)-2-(dimethylamainomethylenyl)-1,3-butandione,
1-(4-nitrophenyl)-2-(dimethylaminomethylenyl)-1,3-butandione,
1-(4-aminophenyl)-2-(dimethylaminomethylenyl)-1,3-butandione,
1-(2,4-dichlorophenyl)-2-(dimethylaminomethylenyl)-1,3-butandione,
1-(4-cyanophenyl)-2-[1-(dimethylamino)ethylidenyl]-1,3-butandione.

PREPARATION OF INTERMEDIATE 5-Acyl-2-(1H)Pyridinones

EXAMPLE 5

5-Acetyl-1,2-dihydro-6-methyl-2-oxo-3-pyridinecarbonitrile

Cyanoacetamide (4.02 g, 0.05 mole) was added to a stirred suspension of sodium hydride (1.2; g, 0.05 mole) in dry tetrahydrofuran (125 ml) under an argon blanket. The suspension was warmed to 50° C., allowed to cool to room temperature and then 3-[(dimethylamino9)-methylenyl]-2,4-pentanedione (7.75 g, 0.050 mole) dissolved in 20 ml of dry THF was added to the suspension. The heterogeneous mixture was heated overnight at 50° C. The reaction mixture was allowed to cool to room temperature and neutralized with acetic acid to PH 6, and concentrated on the rotary evaporator. The residue was extracted with a 50:50 methylene chloride—water mixture and collected by filtration to yield 5.8 g (66%) of a tan solid. Recrystallization from EtOAC (ethyl acetate) gave 3.84 g (44%) of 5-acetyl-1,2-dihydro-6-methyl-2-oxo-3-pyridinecarbonitrile m.pt. 225°–226° C.

In a similar fashion, by modifying the reactants and by substantially following the foregoing procedure there are produced:

5-propionyl-1,2-dihydro-6-methyl-2-oxo-3-pyridinecarbonitrile
5-n-butyroyl-1,2-dihydro-6-methyl-2-oxo-3-pyridinecarbonitrile
5-isobutyroyl-1,2-dihydro-6-methyl-2-oxo-3-pyridinecarbonitrile
5-n-caproyl-1,2-dihydro-6-methyl-2-oxo-3-pyridinecarbonitrile
5-n-heptanoyl-1,2-dihydro-6-methyl-2-oxo-3-pyridinecarbonitrile
5-caproyloyl-1,2-dihydro-6-methyl-2-oxo-3-pyridinecarbonitrile
5-nonyloyl-1,2-dihydro-6-methyl-2-oxo-3-pyridinecarbonitrile and their corresponding 6-ethyl homologs.

EXAMPLE 6

5-Acetyl-1,2-dihydro-2-oxo-6-phenyl-3-pyridinecarbonitrile

Cyanoacetamide (2.50 g, 0.03 mole) was added to a stirred suspension of sodium hydride in (150 ml) THF and warmed to 50° C. The mixture was allowed to cool to room temperature then 3-[(dimethylamino)methylenyl]-1-phenyl-1,3-butanedione (6.52 g, 0.03 mole) dissolved in THF (20 ml) was added all at once. The suspension was heated and stirred at 50° C. overnight. The reaction mixture was allowed to cool to room temperature, treated with acetic acid to pH 6 and concentrated on the rotary evaporator. Workup as in Example 5 gave 3.0 g of a yellow powder. The powder was mixed with 10 g of silica gel (60–200 mesh) and flash chromatographed eluting with 25% EtOAC −75% CH$_2$Cl$_2$ collecting 50 ml fractions to yield 1.1 g of 5-acetyl-1,2-dihydro-2-oxo-6-phenyl-3-pyridinecarbonitrile m.pt. 259°–261° C. in fractions 11 to 20.

EXAMPLE 7

5-Benzoyl-1,2-Dihydro-6-Methyl-2-Oxo-3-pyridinecarbonitrile

The chromatography in Example 6 gave 1.1 g of 5-benzoyl-1,2-dihydro-6-methyl-2-oxo-3-pyridinecarbonitrile in fractions 24 to 40 m.pt. 265°–261° C.

EXAMPLE 8

3-Cyano-1,2-Dihydro-6-Methyl-2-Oxo-5-Pyridinecarboxylic acid ethyl ester

Ethylacetoacetate (6.5 g, .050 mole) and dimethylformamide dimethyl acetal (7.14 g, .060 mole) were stirred together under argon overnight. The resulting reddish oil was concentrated on the rotary evaporator and the concentrate then dissolved in THF (10 ml) and quickly added to a suspension of cyanoacetamide (4.20 g, 0.050 mole) and sodium hydride in THF (175 ml). The reaction mixture was heated and stirred overnight at 50° C. The reaction mixture was neutralized to pH 6 with acetic acid and concentrated on the rotary evaporator. The residue was triturated with a 50:50 CH$_2$Cl$_2$—H$_2$O mixture collected and recrystallized (EtOAC) giving 4.7 g of 3-cyano-1,2-dihydro-6-methyl-2-oxo-5-pyridinecarboxylic acid ethyl ester m.pt. 208°–210° C.

EXAMPLE 9

5-(1-Oxopentyl)-1,2-Dihydro-6-Methyl-2-Oxo-3-Pyridine Carbonitrile

3-[(Dimethylamino)methylenyl]-2,4-octanedione (7.29 g, 0.037 mole) was added to a stirred suspension or cyanoacetamide (3.36 g, 0.04 mole) and sodium hydride (1.0 g, .04 mole) and treated as above, to yield 4.97 g (61%) of an off white power. Approximately 3.0 g of this powder was mixed with 8.0 g of 60–200 mesh silica gel and flash chromatographed eluting with 35% EtOAC −65% CH$_2$Cl$_2$ and collecting 65 ml fractions. 600 mg of 5-(1-oxopentyl)-1,2-dihydro-6-methyl-2-oxo-3-pyridine carbonitrile m.pt. 216°–217° C. was collected in fractions 5 and 6.

EXAMPLE 10

5-Acetyl-1,2-Dihydro-6-Butyl-2-Oxo-3-Pyridinecarbonitrile

The flash chromatography described in Example 9 was continued to give 1.8 g of 5-acetyl-1,2-dihydro-6-butyl-2-oxo-3-pyridine carbonitrile m.pt. 195°–197° C. in fractions 12 to 25.

EXAMPLE 11

5-(1-Oxopropyl)-6-Ethyl-1,2-Dihydro-2-Oxo-3-Pyridinecarbonitrile

4-[(Dimethylamino)methylenyl]-3,5-heptanedione dissolved in THF was added all at once to a suspension of cyanoacetamide (4.21 g, 0.050 mole) and sodium hydride (1.20 g, .050 mole) in dry THF (150 ml) under argon and, with constant stirring, heated at 50° C. overnight. The mixture was brought to pH 6 with acetic acid and concentrated on a rotary evaporator. The residue was recrystallized (methanol) giving 4.0 g (40%) of 5-(1-oxopropyl)-6-ethyl-1,2-dihydro-2-oxo-3-pyridinecarbonitrile m.pt., 247°–248° C.

EXAMPLE 12

6-Ethyl-1,2-Dihydro-5-[(4-Methylthio)benzoyl]-2-Oxo-3-Pyridinecarbonitrile and 5-(1-Oxopropyl)-1,2-Dihydro-6-(4-Methylthiophenyl)-2-Oxo-3-Pyridinecarbonitrile 1-[4-((methylthio)phenyl)]-1,3-pentanedione (2.66 g, 0.12 mole) and dimethylformamide dimethylacetal (1.79 g, 0.015 mole) were stirred overnight at room temperature. The resulting red oil was concentrated on the rotary evaporator and the concentrate was dissolved in THF and added to a suspension of cyanoacetamide (0.84 g, 0.010 mole) and sodium hydride (0.25 g, 0.010 mole) in THF (50 ml), and, with constant stirring heated at 50° C. for 15 hours and cooled. The mixture was brought to pH 6 with acetic acid and concentrated. The residue was dissolved in CH$_2$Cl$_2$, extracted with 5% NaHCO$_3$, washed with brine, separated, dried (MgSO$_4$) and filtered. Concentration on the rotary evaporator gave a yellow gum which upon trituration with Et$_2$O solidified. Recrystallization (EtOAC) gave 1.37 g m.pt. 208°–210° C. The HPLC (u Bondpack CN column, 55% MEOH/45% H$_2$O) showed two peaks in roughly a 40:60 ratio).

EXAMPLE 13

5-Acetyl-6-Methyl-2(1H)-Pyridinone 5-acetyl-1,2-dihydro-6-methyl-2-oxo-3-pyridinecarbonitrile (2.32 g, 0.013 mole) and concentrated HCl (50 ml) were heated and stirred at reflux under an argon atmosphere for 5 hours. Upon cooling to room temperature a solid precipitated. The solid was collected by filtration and allowed to air dry. The dry solid (1.25 g) was heated to 280°–290° C. and maintained at this temperature for 7 minutes. The residue was allowed to cool to room temperature then extracted into methylene chloride. Concentration of the methylene chloride solution followed by flash chromatography (50% methylene chloride—ethyl acetate) gave .46 g m.pt. 201°–202° C. (1:t 196°–198° C.).

EXAMPLE 14

5-Acetyl-1,2-Dihydro-6-Methyl-2-Oxo-3-Pyridinecarboxylic Acid

To 100 ml 6 N hydrochloric acid is added 5.0 grams (0.028 mole) of 5-acetyl-1,2-dihydro-6-methyl-2-oxo-3-pyridinecarbonitrile. The mixture is stirred and refluxed for 20 hours. Evaporation of the solvent affords the title compound.

EXAMPLE 15

5-Acetyl-1,2-Dihydro-6-Methyl-2-Oxo-3-Pyridinecarboxylic Acid Ethylester

In 500 ml absolute alcohol is dissolved 5 grams 5-acetyl-1,2-dihydro-6-methyl-2-oxo-3-pyridinecarboxylic acid. The mixture is stirred and refluxed while a slow stream of dry hydrogen chloride is introduced. The reaction is allowed to proceed for 7 hours after which the solvent is evaporated and the residue is recrystallized from alcohol to give the title compound.

EXAMPLE 16

5-Acetyl-1,2-Dihydro-6-Methyl-2-Oxo-3-Pyridinecarboxamide

To 100 grams of concentrated sulfuric acid is added 10 g (0.056 mole) of 5-acetyl-1,2-dihydro-6-methyl-2-oxo-3-pyridinecarbonitrile. The mixture is stirred at 60° C. for 5 hours, cooled and then poured on 1 kg ice. The resulting solid is collected, washed with water and recrystallized from ethanol to give the title compound.

EXAMPLE 17

5-Acetyl-1,2-Dihydro-6-Methyl-2-Oxo-3-Aminopyridine Hydrochloride

A solution of 10.2 g of potassium hydroxide and 10.8 g of bromine in 100 ml of water is stirred with 11.6 g (0.06 mole) of 5-Acetyl-1,2-dihydro-6-methyl-2-oxo-3-pyridine carboxamide. The mixture is heated to 60° C. for 1 hour and then treated with 14.4 g of potassium hydroxide in 25 ml water and heated to 75° C. for 1 hour and cooled to 0° C. The (free base) title compound precipitates, is collected and washed with water. The material is suspended in ether and treated with dry hydrogen chloride gas to form the HCl salt.

EXAMPLE 18

3,6-Dimethyl-5-Acetyl-1,2-Dihydro-3-2-oxo-pyridine

Step A:

5-Acetylethyleneketal-1,2-Dihydro-6-methyl-2-oxo-3-pyridinecarboxaldehyde

To toluene (100 ml) add 5-acetyl-1,2-dihydro-6-methyl-2-oxo-3-pyridinecarbonitrile (17.6 g/0.1 mol), thyleneglycol (6.2 g/0.1 mol) and p-toluenesulfonic acid (0.1 g), and heat, under reflux conditions, the resulting mixture until the theoretical amount of water is distilled. Cool and wash the solvent with sodium bicarbonate solution. Dry (with sodium sulfate) and evaporate the solvent and dissolve the residue in 100 ml THF. The resulting solution is treated at room temperature with diisobutylaluminum hydride (0.1 mol) for one hour and the reaction mixture quenched with water and extracted with ether. The ether extract is water-washed, dried and evaporation of the solvent yields the desired product of this step.

Step B:

5-Acetyl-1,2-dihydro-3,6-dimethyl-2-oxo-pyridine

In 150 ml of ethanol, dissolve 10 g (0.045 mol) of the produce of Step A and 1.0 g of 10% palladium on carbon. The resulting mixture is hydrogenated at 50° C. until 2 equivalents of hydrogen gas is taken up. The solution is filtered and the solvent is treated with 150 ml 6N hydrochloric acid and heated to reflux for one hour. Evaporation of the solvent yields the desired compound of this example.

EXAMPLE 19

5-Acetyl-1,2-Dihydro-3-Propyl-6-Methyl-2-oxopyridine

In 200 ml of THF is dissolved 10 g (0.045 mol) of 5-acetylethyleneketal-1,2-dihydro-6-methyl-2-oxo-3-pyridinecarboxaldehyde, and to this solution is added 0.090 ml of ethylmagnesium bromide in dimethylether and the solution is refluxed for two hours, quenched with 10% $NH_4Cl$ solution. The aqueous phase is discarded, and the organic phase water-washed, dried ($Na_2SO_4$), evaporated and the residue dissolved in 200 ml ethyl alcohol. 10% palladium on carbon was added and the mixture hydrogenated at 50° C. until one equivalent of hydrogen ($\simeq 1$ hour) is taken up. The solution is filtered, and the solvent is treated with 150 ml 6N HCl and heated to reflux for one hour. Evaporation of the solvent yields the desired compound of this example.

EXAMPLE 20

1,2-Dihydro-5-[1-(Methoxyimino)ethyl]-6-Methyl-2-oxo-3-pyridinecarbonitrile

A mixture of 5-acetyl-6-methyl-2(1H)pyridinone (1.76 g, 0.010 mol), methoxyamine hydrochloride (0.90 g, 0.107 mol) and pyridine (5.0 ml) were heated and stirred in EtOH (150 ml) at reflux. The initially heterogeneous mixture cleared as everything went into solution. At the end of 2 hours a solid precipitated. The reaction mixture was allowed to cool to room temperature and the solid was collected by filtration. Recrystallization (EtOH) gave 0.70 g (35%) m.pt. 275°–285° C.

EXAMPLE 21

1,2-Dihydro-5-[1-(methoxyimino)pentyl]-6-methyl-2-oxo-3-pyridinecarbonitrile

A mixture of 1,2-dihydro-6-methyl-2-oxo-5-(1-oxopentyl)-3-pyridinecarbonitrile (0.70 g, 0.0032 mol), methoxyamine hydrochloride (0.32 g, 0.0038 mol) and pyridine (2.0 ml) were heated and stirred at reflux in EtOH (30 ml) overnight. The solution was cooled to room temperature and concentrated on the rotary evaporator. The residue was diluted with $H_2O$ and the resulting solid collected by filtration. Recrystallization (MeOH-$H_2O$) gave 0.38 g (48%) m.pt. 159–161.

EXAMPLE 22

1,2-Dihydro-5-[1-(Methoxyimino)hexyl]-6-methyl-2-oxo-3-pyridinecarbonitrile

A mixture of 1,2-dihydro-6-methyl-2-oxo-5-(1-oxohexyl)-3-pyridinecarbonitrile (0.80 g, 0.0034 mol), methoxyamine hydrochloride (0.32 g, .0038 mol) and pyridine (2.0 ml) were heated and stirred at reflux overnight in EtOH (30.0 ml). The solution was allowed to cool to room temperature and the solvent was removed on the rotary evaporator. The pasty residue was triturated with $H_2O$, filtered and recrystallized (EtOH-$H_2O$) giving 0.5 g (56%) m.pt. 159°–165° C. One more recrystallization gave the analytical sample m.pt. 170°–171° C.

EXAMPLE 23

6-Ethyl-5-[1-(Methoxyimino)propyl]-2(1H)-pyridinone

A mixture of 5-ethyl-5-(1-oxopropyl)-2-(1H)-pyridinone (1.0 g, 0.0056 mol), methoxyamine hydrochloride (0.53 g, 0.0063 mol) and pyridine (3.0 ml) were heated and stirred at reflux for 48 hours in EtOH (30 ml). The reaction mixture was allowed to cool to room temperature and concentrated to a viscous liquid on the rotary evaporator at 60° C. The residue solidified on cooling. The solid was triturated with $H_2O$ (50 ml) and then collected by filtration to give 0.91 g, m.pt. 120°–125° C. One recrystallization (EtOH-$H_2O$) gave 0.55 g (47%), m.pt. 129°–131° C.

In a similar manner, by substituting the reactants of Examples 20–23 with the equivalent amounts of the appropriate alkoxyamine and the appropriate 5-acyl-1,2-6-($R_6$)-2-oxo-pyridinone (particularly those prepared in Examples 1-19) and by substantially following the procedure of Examples 20-23 there may be produced the desired alkoxyimino ethers of Formula I and in particular the following compounds:

1,2-dihydro-5-[1-(methoxyimino)ethyl]-6-ethyl-2-oxo-3-pyridinecarbonitrile;
1,2-dihydro-5-[1-(methoxyimino)butyl]-6-ethyl-2-oxo-3-pyridinecarbonitrile;
1,2-dihydro-5-[1-(methoxyimino)pentyl]-6-ethyl-2-oxo-3-pyridinecarbonitrile;
1,2-dihydro-5-[1-(methoxyimino)hexyl]-6-ethyl-2-oxo-3-pyridinecarbonitrile;
1,2-dihydro-5-[1-(methoxyimino)ethyl]-6-methyl-2-oxo-3-pyridinecarbonitrile;
1,2-dihydro-5-[1-(methoxyimino)propyl]-6-methyl-2-oxo-3-pyridinecarbonitrile;
1,2-dihydro-5-[1-(methoxyimino)butyl]-6-methyl-2-oxo-3-pyridinecarbonitrile.

as well as the ethoxyimino, propoxyimino, butyroxyimino, homologs of the foregoing and the 3-position carboxylic acid, carboxylic acid alkyl ester, carbamate, amino, 3-hydrogen and 3-lower alkyl analogs (i.e., 3-pyridinecarboxylic acid ethyl esters, 3-pyridinecarboxamides, 3-aminopyridines, pyridine and 3-alkylpyridine) of the foregoing.

The compounds of general Formula 1 may be used in the treatment of cardiac failure including congestive heart failure, backward heart failure, forward heart failure, left ventricular heart failure, or right ventricular heart failure or in the treatment of any other condition which requires the strengthening of heart action with a cardiotonic.

The utility of Formula 1 compounds as cardiotonics may be determined by administering the test compound (0.01-0.3 mg/kg) intravenously, intraperitoneally, intraduodenally or intragastrically in a suitable vehicle to a mongrel dog (either sex). The test dogs are anesthetized and prepared by isolating a suitable artery (e.g., femoral or common carotid) and vein (e.g., femoral or external jugular) introducing polyethylene catheters filled with 0.1% Heparin-Na to record arterial blood pressure and administer compounds, respectively. The chest is opened by splitting the sternum at the midline or by an incision at the left fifth intercostal space, and a pericardial cradle is formed to support the heart. A Walton-Brodie strain gage is sutured to the right or left ventricle to monitor myocardial contractile force. An electromagnetic flow probe may be placed around the root of the ascending aorta for measuring cardiac output less coronary blood flow. Heart failure is induced by administering sodium pentobarbital (20 to 40 mg/kg) followed by a continuous infusion of 1-2 mg/kg/min. or propranalol hydrochloride (4 mg/kg) followed by a continuous infusion of 0.18 mg/kg/min. to the blood perfusing the heart. Following administration of either of these cardiac depressants, the right atrial pressure dramatically increases and cardiac output is severely depressed. Reversal of these effects by the test compound indicates cardiotonic activity.

The compounds may be administered in various manners to achieve the desired effect. The compounds may be administered alone or in the form of pharmaceutical preparations to the patient being treated either orally or parenterally, that is, intravenously or intramuscularly. The amount of compound administered will vary with the patient, the severity of the cardiac failure and the mode of administration.

For oral or parenteral administration the cardiotonically effective amount of compound is from about 0.01 mg/kg of patients body weight per day up to about 100 mg/kg of patient body weight per day and preferably from about 0.01 mg/kg of patient body weight per day up to about 50 mg/kg of patient body weight per day.

For oral administration a unit dosage may contain, for example, from 0.1 to 750 mg of the active ingredient, preferably about 0.5 to 500 mg of the active ingredient. For parenteral administration a unit dosage may contain, for example, from 0.1 to 250 mg of the active ingredient, preferably about 0.5 to 100. Repetitive daily administration of the compounds may be desired and will vary with the condition of the patient and the mode of administration.

As used herein the term patient is taken to mean warm blooded animals, for example, birds, such as chickens and turkeys, and mammals, such as primates, humans, sheep, horses, bovine cows and bulls, pigs, dogs, cats, rats and mice.

For oral administration the compounds can be formulated into solid or liquid preparations such as capsules, pills, tablets, troches, powders, solutions, suspensions or emulsions. The solid unit dosage forms can be a capsule which can be of the ordinary gelatin type containing, for example, lubricants and inert filler, such as lactose, sucrose and cornstarch. In another embodiment the compounds of general Formula 1 can be tableted with conventional tablet bases such as lactose, sucrose and cornstarch in combination with binders, such as acacia, cornstarch or gelatin, disintegrating agents such as potato starch or alginic acid, and a lubricant such as stearic acid or magnesium stearate.

For parenteral administration the compounds may be administered as injectable dosages of a solution or suspension of the compound in a physiologically acceptable diluent with a pharmaceutical carrier which can be a sterile liquid such as water, alcohols, oils and other acceptable organic solvents with or without the addition of a surfactant and other pharmaceutically acceptable adjuvants. Illustrative of oils which can be employed in these preparations are those of petroleum, animal, vegetable, or synthetic origin, for example, peanut oil, soybean oil and mineral oil. In general, water, saline, aqueous dextrose and related sugar solutions, ethanol and glycols such as propylene glycol or polyethylene glycol or 2-pyrrolidone are preferred liquid carriers, particularly for injectable solutions.

The compounds can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, a silicone rubber manufactured by the Dow-Corning Corporation.

As is true in many large classes of compounds certain subgeneric members and certain specific members of the class are preferred for the pharmaceutical activity in treating disease states in man. In this instance the preferred compounds of formula I are those wherein $R_5$ is lower alkyl. The preferred $R_3$ substituent is cyano, hydrogen, lower alkyl or amino. The preferred $R_4$ substituent is hydrogen, the preferred $R_6$ substituents are either ethyl or methyl and the preferred $R_1$ is methyl or ethyl. The preferred compounds are those wherein $R_3$ is hydrogen or cyano, R₄ is hydrogen, R₆ is methyl or ethyl and R₅ is any straight chain hydrocarbyl radical, and R₁ is methyl and ethyl with the specific compounds most preferred being:

1,2-dihydro-5-[1-(methoxyimino)ethyl]-6-methyl-2-oxo-3-pyridinecarbonitrile;
1,2-dihydro-5-[1-(methoxyimino)propyl]-6-methyl-2-oxo-3-pyridinecarbonitrile;
1,2-dihydro-5-[1-(methoxyimino)butyl]-6-methyl-2-oxo-3-pyridinecarbonitrile;
1,2-dihydro-5-[1-(methoxyimino)pentyl]-6-methyl-2-oxo-3-pyridinecarbonitrile;
1,2-dihydro-5-[1-(methoxyimino)hexyl]-6-methyl-2-oxo-3-pyridinecarbonitrile;
1,2-dihydro-5-[1-(methoxyimino)heptanyl]-6-methyl-2-oxo-3-pyridinecarbonitrile;
1,2-dihydro-5-[1-(methoxyimino)ethyl]-6-ethyl-2-oxo-3-pyridinecarbonitrile;
1,2-dihydro-5-[1-(methoxyimino)propyl]-6-ethyl-2-oxo-3-pyridinecarbonitrile;
1,2-dihydro-5-[1-(methoxyimino)butyl]-6-ethyl-2-oxo-3-pyridinecarbonitrile;
1,2-dihydro-5-[1-(methoxyimino)pentyl]-6-ethyl-2-oxo-3-pyridinecarbonitrile;
1,2-dihydro-5-[1-(methoxyimino)heptanyl]-6-ethyl-2-oxo-3-pyridinecarbonitrile, and the 3H analogs (i.e., the 1,2-dihydro-5-[alkoxyimino)alkyl]-6-alkyl-2-(1H)-pyridinones) of the foregoing specific compounds.

We claim:

1. A compound of the formula

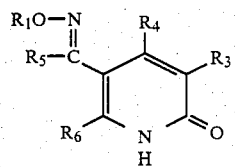

or a pharmaceutically acceptable salt thereof, wherein
R₁ is $C_{1-10}$ alkyl,
R₃ is H, lower alkyl, —C≡N, -NH₂, —CONH₂ or —COOR with R being hydrogen or lower alkyl,
R₄ is hydrogen or lower alkyl,
R₅ is $C_{1-10}$ alkyl, phenyl, X-substituted phenyl, hydroxy or lower alkoxy, and X is lower alkyl, lower alkoxy, lower alkylthio, lower alkylsufonyl, lower alkylsulfoxyl, halogen, nitro, lower alkanoyl, alkoxycarbonyl, carboxy, cyano, NH₂, CONH₂, amidino, imidazol-2-yl, or CF₃,
R₆ is hydrogen, $C_{1-10}$ alkyl, phenyl X-substituted phenyl, hydroxy or lower alkoxy, and X is lower alkyl, lower alkoxy, lower alkylthio, lower alkylsulfonyl, lower alkylsulfoxyl, halogen, nitro, lower alkanoyl, alkoxy carbonyl, carboxy, cyano, NH₂, CONH₂, amidino, imidazol-2-yl, or CF₃.

2. A compound of claim 1 wherein R₃ is cyano.
3. A compound of claim 1 wherein R₄ is hydrogen.
4. A compound of claim 2 wherein R₁ is methyl.
5. A compound of claim 2 wherein R₆ is methyl.
6. A compound of claim 2 wherein R₆ is ethyl.

* * * * *